United States Patent [19]
Lee et al.

[11] Patent Number: 5,475,139
[45] Date of Patent: Dec. 12, 1995

[54] METHOD FOR THE PREPARATION OF SUBSTITUTED DERIVATIVES OF DIPHENYL AMINE

[75] Inventors: Fangchen Lee; Tsung-Chung Liu, both of Tachia Taichung, Taiwan

[73] Assignee: Yung Shin Pharm. Ind. Co., Ltd., Tachia Taichung, Taiwan

[21] Appl. No.: 139,697

[22] Filed: Oct. 22, 1993

[51] Int. Cl.⁶ .................................................. C07C 209/58
[52] U.S. Cl. ........................... 564/414; 564/433; 564/434
[58] Field of Search .................................... 564/414, 433, 564/434

[56] References Cited

U.S. PATENT DOCUMENTS

| | | | |
|---|---|---|---|
| 3,536,758 | 10/1970 | Sallmann et al. | 260/558 |
| 3,558,690 | 1/1971 | Sallmann et al. | 260/471 |
| 4,057,581 | 11/1977 | Krall et al. | 564/433 |
| 4,299,983 | 11/1981 | Martin et al. | 564/433 |
| 5,006,561 | 4/1991 | Arrowsmith et al. | 514/605 |

FOREIGN PATENT DOCUMENTS 2-215750  8/1990  Japan .

*Primary Examiner*—Peter O'Sullivan

[57] ABSTRACT

This invention provides a novel process for the preparation of substituted derivatives of diphenyl amine. The special feature of this novel process is that low cost and recoverable phenolic salts are used as catalysts for molecular rearrangement and aminolysis to obtain substituted derivatives of diphenyl amine in high yield.

9 Claims, No Drawings

METHOD FOR THE PREPARATION OF SUBSTITUTED DERIVATIVES OF DIPHENYL AMINE

DESCRIPTION OF THE INVENTIONS

1. Background Art

The condensation of phenylamine and halobenzene in the Ullmann reaction is the most common method for the preparation of substituted derivatives of diphenyl amine. The reaction must be carried out at high temperature for a long period of time and the isolation and purification of the reaction product is cumbersome. The Chapman reaction is an alternative method for the preparation of substituted derivatives of diphenyl amine. According to the Chapman reaction, an arylamide (formula B of FIG. 1) is produced from an aryl imino ester (formula A of FIG. 1) by intramolecular nucleophilic attack followed by a rearrangement at 180°–230° C. However, the product of Chapman reaction has to be hydrolyzed further at high temperature to obtain substituted derivatives of diphenyl amine, which are important raw materials for pharmaceuticals, plastics, food and dye industries. The high cost of substituted derivatives of diphenyl amine resulting from the long process time and high reaction temperature is the common disadvantage shared by these two traditional methods.

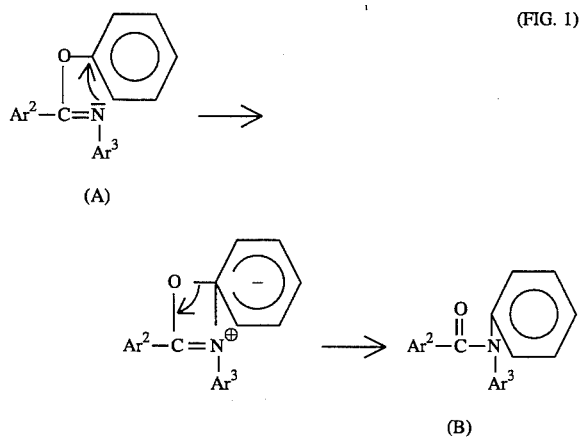

(FIG. 1)

2. Disclosure of the Invention

According to the present invention, substituted derivatives of diphenyl amine are prepared from N-phenyl phenoxy acetamide and metallic phenol salts undergoing the intramolecular nucleophilic attack and aminolysis. The reactants, N-phenyl phenoxy acetamide, may have mono- or multi-substitutions of halogen, $C_{1-4}$ alkyl group and hydrogen in the phenoxy group. The N-phenyl phenoxy acetamide are also prepared from metallic phenol salts in an inert solvent through the alkylation with halides of N-phenyl acetamide in that the N-phenyl group may have mono- or multi-substitutions of halogen, $C_{1-4}$ alkyl group or hydrogen.

In this invention the metallic phenol salts of Na, K, Mg, etc., which act as catalysts, may have mono- or multi-substitutions of $C_{1-4}$ alkyl, amino, methoxy . . . groups on their phenyl rings. In general, the metallic phenol salts substituted with electron-donating groups are the proper catalysts for the preparation of substituted derivatives of diphenyl amine. Metallic phenol salts substituted with three alkyl or amino groups have better catalytic effects.

Details for the preparation of substituted derivatives of diphenyl amine are further disclosed as followings. The raw materials, N-phenyl phenoxy acetamide are dissolved in polar aprotic solvents, such as N,N-dimethylformamide, N,N-dimethylacetamide, hexamethylphosphoramide, dioxane, acetonitrile, etc., followed by the addition of metallic phenol salts substituted with different electron-donating groups. The mixture is heated to 80°–160° C. to induce a Chapman-like rearrangement, i.e., a rearrangement occurring when an intramolecular nucleophilic substitution takes place. After that, aminolysis proceeds directly in the presence of sufficient metallic phenol salt as catalyst. Increased reactivity and improved yield are observed when the N-phenyl group of the raw materials is substituted with electron-donating groups, such as alkyl, amino, etc., and the other phenoxyl group is substituted with electron-withdrawing groups, such as halide, ester, etc. Especially superior results are obtained with polar aprotic dimethyl formamide and dimethyl acetamide as solvents. The optimum temperature for the reaction is 120°–150° C.

Substituted derivatives of diphenyl amine obtained according to the above procedures are extracted with organic solvents or recovered directly with distillation under reduced pressure in high yield. The remaining metallic phenol salt are recoverd with water dissolution, acidification and organic solvent (chloroform, toluene, etc.) extraction for reuse. The recovery yield is as high as 95–99%. The method for the preparation of substituted derivatives of diphenyl amine disclosed in this invention not only has a high product yield, but also recovers the catalyst efficiently. Thus, this novel method is effective in lowering the industrial production cost of substituted derivatives of diphenyl amine and reducing the environmental pollution caused by the process wastewater discharge.

The method for the preparation of substituted derivatives of diphenyl amine disclosed in this invention is schemetically shown in the following diagram. The raw materials, N-phenyl phenoxy acetamide (formula II) are dissolved in polar aprotic solvents, followed by the addition of metallic phenol salts (formula III) and heated to a proper temperature to induce a Chapman-like rearrangement. The rearrangement results in the formation of an intermediate compound (formula IV), which then undergoes direct aminolysis to form the substituted derivative products of diphenyl amine (formula I) in the presence of sufficient metallic phenol salt as catalyst. In this schematic diagram, $Y_1$, $Y_2$ and $Y_3$ are same or different and each represents a halogen, C1-4 alkyl group or hydrogen; $Z_1$, $Z_2$ and $Z_3$ are same or different and each represents a $C_{1-4}$ alkyl group, $R_1$, $R_2$ and $R_3$ are same or different and each represents a $C_{1-4}$ alkyl group, amino group, and methoxy group, and M represents metals such as Na, K, Mg, . . . etc.

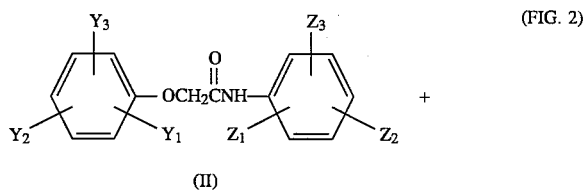

(FIG. 2)

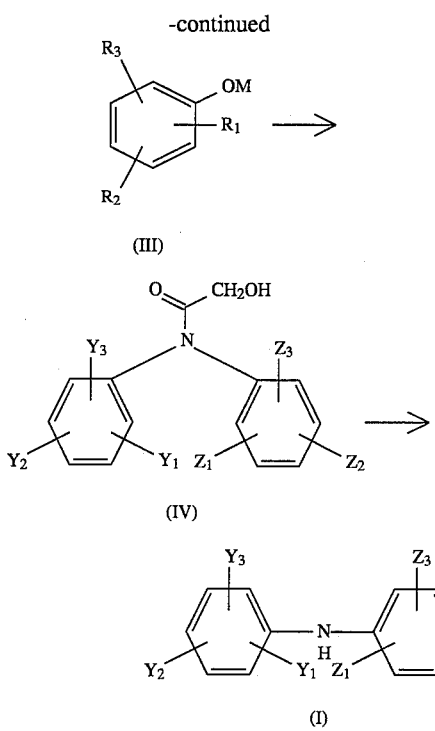

(III)

(IV)

(I)

The raw materials, N-phenyl phenoxy acetamide (formula II) may be prepared from treating phenols (with Y substitutes, formula V) with alkaline metal, such as NaOH, NaO, KOH, $Na_2CO_3$, $K_2CO3$, etc., in an inert solvent, such as toluene, benzene-, halobenzene, etc., to obtain metallic phenol salts (with Y substitutes, formula VIII), which is then alkylated with halides of N-phenyl acetamide (with Z substitutes, formula VI) at a proper temperature of 80°–110° C. $Y_1$, $Y_2$ and $Y_3$ are same or different and each represents a halogen, C1–4 alkyl group or hydrogen, $Z_1$, $Z_2$ and $Z_3$ are same or different and each represents a $C_{1-4}$ alkyl group, $R_1$, $R_2$ and $R_3$ are same or different and each represents a $C_{1-4}$ alkyl group, amino group, and methoxy group, and M represents metals such as Na, K, Mg, etc., and X represents halogen atom such as Cl, Br and I.

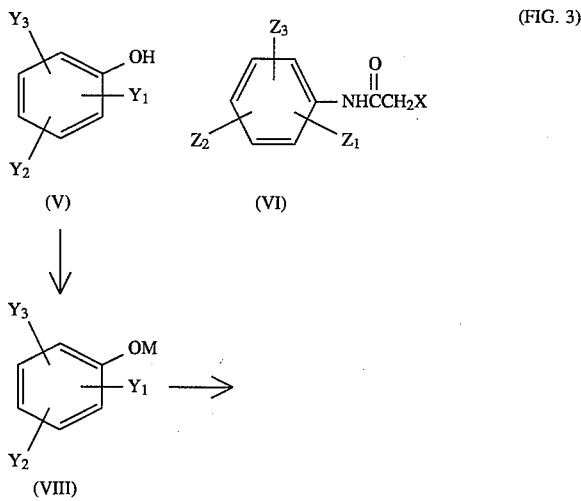

(FIG. 3)

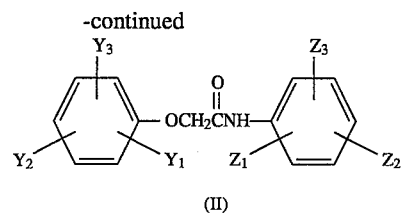

(II)

The catalysts, metallic phenol salts (with R substitutes, formula III) may be prepared from reacting phenols (with R substitutes, formula VII) and alkaline metal, such as NaOH, NaO, KOH, $Na_2CO3$, $K_2CO3$ . . . etc., in an inert solvent, such as toluene, benzene, halobenzene, . . . etc. $R_1$, $R_2$ and $R_3$ are same or different and each represents a $C_{1-4}$ alkyl group, amino group, and methoxy group, and M represents metals such as Na, K, Mg, . . . etc.

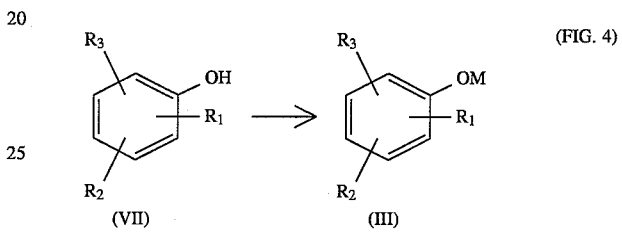

(FIG. 4)

The invention is illustrated by, but not limited by, the following examples.

EXAMPLE 1

Preparation of N-phenyl 2,6-dichloroaniline 37.6 g of 2,4,6-trimethyl phenol and 11 g of sodium hydroxide were dissolved in 30 ml of water and mixed with 150 ml of toluene. The toluene recovered from heating was mixed with 139 ml of N,N-dimethylformamide to obtain a N,N-dimethylformamide solution. 40 g of 2,6-dichlorophenol was dissolved in 130 ml of toluene, followed by the addition of 9.8 g of sodium hydroxide in 20 ml of water, 41.5 g of N-phenyl chloroacetamide and 8.7 ml of N,N-dimethylformamide, and refluxed in a oil bath at 140°–150° C. for 15 h. The toluene was recovered from the reflux, and mixed with the above N,N-dimethylformamide solution and reacted for 3 h. Recovering N,N-dimethylformamide from the reacted mixture with distillation under reduced pressure (145°–150° C., 8 mm Hg) resulted in the formation of 53 g of N-phenyl 2,6-dichloroaniline and the product yield was 90.75%.

Recovery of 36.9 g of 2,4,6-trimethyl phenol was achieved by dissolving the residues with 150 ml of water and acidifying to pH 5–6 with hydrochloric acid. The recovery yield of 2,4,6-trimethyl phenol was 98.2%.

The physical data of N-phenyl 2,6-dichloroaniline are $H^1$-NMR(DMSO-d6): δ7.87 (1H, S, Ar-NH), δ7.55 (2H, d, J=8 Hz, H-3, H-5), δ7.26 (1H, t, J=8.5 Hz, H-4), δ7.12 (2H, t, J=8.2 Hz, H-3', H-5'), δ6.70 (1H, d, J=7.4 Hz, H-4'), δ6.52 (2H, d, J=7.62 Hz). IR (KBr, $cm^{-1}$): 3400, 1600, 1500. UV $\lambda_{max}$ nm: ($CH_3OH$) 283 nm. M.P.: 48°–49° C.

EXAMPLES 2–6

Preparation of N-phenyl 2,6-dichloroaniline

N-phenyl 2,6-dichloroaniline was prepared according to the method of example 1 except that different catalysts were employed. The yields of N-phenyl 2,6-dichloroaniline from different catalysts are shown in Table 1.

| Example No. | Catalyst | Organic Solvent | Yield |
|---|---|---|---|
| 1 | 2,4,6-trimethylphenol | N,N-dimethylformamide | 90.7% |
| 2 | phenol | N,N-dimethylformamide | 93.8% |
| 3 | 4-methylphenol | N,N-dimethylformamide | 86.5% |
| 4 | 4-aminophenol | N,N-dimethylformamide | 85.0% |
| 5 | 4-methoxyphenol | N,N-dimethylformamide | 50.0% |
| 6 | 2,4,6-trichlorophenol | N,N-dimethylformamide | 20.5% |

EXAMPLE 7

Preparation of 2',6'-dichlorophenyl 2-methylphenyl amine

According to method illustrated in the example 1, 2,6-dichlorophenol, toluene and sodium hydroxide were mixed with 45 g of 2-methyl-N-phenyl chloroacetamide and N,N-dimethylformamide, then refluxed in an oil bath. The toluene recovered from the reflux was mixed and reacted with N,N-dimethylformamide solution prepared in advance. The reacted mixture was washed twice with water. 45 g of 2',6'-dichlorophenyl 2-methylphenyl amine was obtained when the toluene layer was dehydrated with magnesium sulfate, then concentrated. The product yield was 72.7%.

Recovery of 32.9 g of 2,6-dimethylphenol was achieved by acidifying the water layer with 6N hydrochloric acid. The recovery yield was 97.62%.

The physical data of 2',6'-dichlorophenyl 2-methylphenyl amine are $H^1$-NMR(200 MHz, $CD_3OD$-d4): $\delta 7.44$ (2H, d, J=8.2 Hz, H-3', H-5'), $\delta 7.07$–7.15 (2H, m, H-4', H-5), $\delta 6.88$–7.07 (1H, m, H-3), $\delta 6.23$–6.79 (1H, m, H-4), $\delta 6.19$–6.23 (1H, m, H-6), $\delta 2.32$ (3H, s). IR (KBr): 3425, 1600, 1505 $cm^{-1}$. M.P.: 46° C.

EXAMPLE 8

Preparation of ethyl 4-phenylaminobenzoate 30.2 g of 4-aminophenol was dissolved in 130 ml of N,N-dimethylformamide, followed by the addition of 11.64 g of 57% NaH and agitated at room temperature for 30 rain to obtain a N,N-dimethylformamide solution. 130 ml of toluene and 10.5 g of 57% NaH were added to 41 g of 4-hydroxy ethylbenzoate. After agitation, 45 g of N-phenyl chloroacetamide and 8.7 ml of N,N-dimethylformamide were also added. The toluene recovered from the reflux was reacted with the above N,N-dimethylformamide solution. After that, the N,N-dimethylformamide was recovered and extracted with toluene. 47 g of ethyl 4-phenylaminobenzoate was obtained when the toluene layer of the extraction process was dehydrated with magnesium sulfate. The product yield was 79%.

The physical data of ethyl 4-phenylaminobenzoate are $H^1$-NMR(200 MHz, $CDCl_3$): $\delta 7.90$–7.94 (2H, m, H-2, H-6), $\delta 6.97$–7.38 (7H, m), $\delta 6.07$ (1H, s, Ar-NH), $\delta 4.34$ (2H, q, J=7.12 Hz), $\delta 1.37$ (3H, t, J=7.1 Hz). IR (KBr): 3350, 1690, 1600, 1530 $cm^{-1}$. M.P.: 105° C.

Those skilled in the art will recognize, or be able to ascertain using no more that routine experimentation, many equivalents to the specific embodiments of the invention described herein. Such equivalents are intended to be encompassed by the following claims.

We claim:
1. A method for the preparation of substituted derivatives of diphenyl amine having the structure of formula I

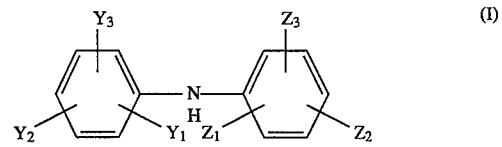

comprising:
(a) dissolving an N-phenyl phenoxy acetamide having the structure of formula (II) in a polar aprotic solvent

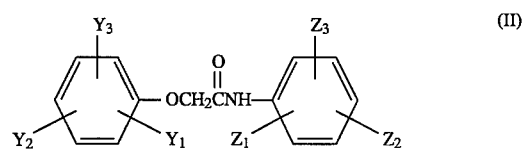

(b) adding at least one metallic phenol salt having the structure of formula (III) and reacting at reaction temperature,

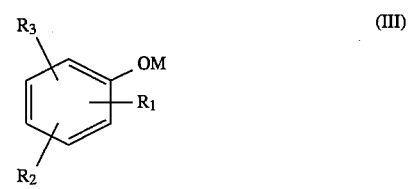

wherein $Y_1$, $Y_2$ and $Y_3$ are same or different and each individually represents a halogen; $C_{1-4}$ alkyl group or hydrogen, $Z_1$, $Z_2$, and $Z_3$ are same or different and each individually represents a $C_{1-4}$ alkyl group; $R_1$, $R_2$ and $R_3$ are same or different and each individually represents a $C_{1-4}$ alkyl group, amino group, and methoxy group, and M represents an alkali metal.

2. The method of claim 1, wherein M is selected from the group consisting of Na, K and Mg.

3. The method of claim 1, wherein said compounds having the structure of formula II are prepared from metallic phenol salts having the structure of formula VIII

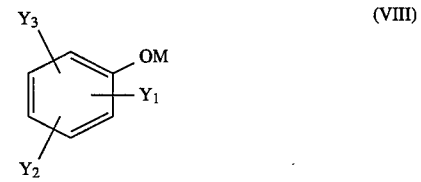

and halides of N-phenyl acetamide having the structure of formula VI

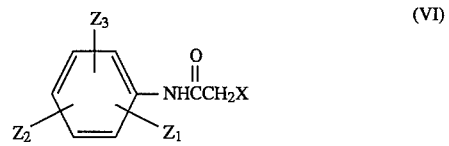

wherein $Y_1$, $Y_2$, $Y_3$, $Z_1$, $Z_2$, $Z_3$, $R_1$, $R_2$, $R_3$ and M are as set forth in claim 1 and X represents a halogen atom.

4. The method of claim 2, wherein M is selected from the group consisting of Na, K and Mg.

5. The method of claim 1, wherein said compounds having the structure of formula II are prepared from metallic phenol salts having the structure of formula VIII,

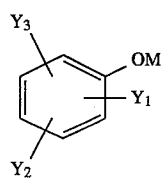

(VIII)

which are reacted with halides of N-phenyl acetamide having the structure of formula VI,

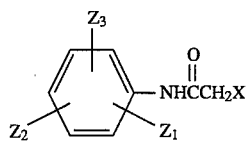

(VI)

said metallic phenol salts having the structure of formula VIII being prepared from phenols having the structure of formula V and alkaline metals,

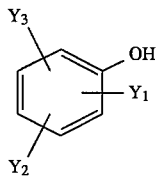

(V)

wherein $Y_1$, $Y_2$, $Y_3$, $Z_1$, $Z_2$, $Z_3$, $R_1$, $R_2$, $R_3$ and M are as set forth in claim 1 and X represents a halogen atom.

6. The method of claim 1, wherein the compounds having the structure of formula III are prepared from phenols having the structure of formula VII and alkaline metals,

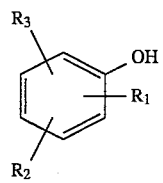

(VII)

wherein $R_1$, $R_2$, $R_3$ and M are as set forth in claim 1.

7. The method claim 1, wherein Rs, Ys and Zs in the formulae represent trisubstitution of at least one phenyl moiety with halogen, $C_{1-4}$ alkyl, amino or methoxy groups.

8. The method claim 1, wherein Rs, Ys and Zs in the formulae represent bisubstitution of at least one phenyl moiety with halogen, $C_{1-4}$ alkyl, amino or methoxy groups.

9. The method claim 1, wherein Rs, Ys and Zs in the formulae represent monosubstitution of at least one phenyl moiety with halogen, $C_{1-4}$ alkyl, amino or methoxy groups.

\* \* \* \* \*